United States Patent [19]

Takita et al.

[11] Patent Number: 4,841,097

[45] Date of Patent: Jun. 20, 1989

[54] DIALKANOYLOXYBENZYLIDENE DIALKANOATE

[75] Inventors: Hitoshi Takita; Fumihiko Kimura; Sakuo Noda, all of Tokyo; Yutaka Mukaida, Moroyama; Toyohiko Nitta; Hidetoshi Kobayashi, both of Tokyo, all of Japan

[73] Assignee: Kureha Kagaku Kogyo Kabushiki Kaisha, Tokyo, Japan

[21] Appl. No.: 181,177

[22] Filed: Apr. 13, 1988

Related U.S. Application Data

[62] Division of Ser. No. 681,289, Dec. 13, 1984, abandoned.

[30] Foreign Application Priority Data

Dec. 26, 1983 [JP] Japan ............................... 58-251692
Jun. 22, 1984 [JP] Japan ............................... 59-128789

[51] Int. Cl.⁴ .................... C07C 69/035; C07C 67/08; C09F 5/08

[52] U.S. Cl. .................................... 560/144; 560/238; 260/410.5

[58] Field of Search .............................. 560/144, 238; 260/410.5

[56] References Cited

U.S. PATENT DOCUMENTS

| | | | |
|---|---|---|---|
| 2,265,141 | 12/1941 | | 560/140 |
| 2,748,160 | 5/1956 | | 560/144 |
| 2,903,444 | 9/1959 | | 560/144 |
| 4,377,594 | 3/1983 | Takita et al. | 424/309 |
| 4,382,955 | 5/1983 | Takita et al. | 424/309 |
| 4,387,102 | 6/1983 | Takita et al. | 424/282 |
| 4,409,240 | 10/1983 | Takita et al. | 424/319 |
| 4,464,396 | 8/1984 | Takita et al. | 424/319 |
| 4,578,404 | 3/1986 | Takita et al. | 514/567 |
| 4,725,598 | 2/1988 | Takita et al. | 514/255 |

FOREIGN PATENT DOCUMENTS

| | | |
|---|---|---|
| 668388 | 12/1965 | Belgium . |
| 55-51018 | 4/1980 | Japan . |
| 57-59807 | 4/1982 | Japan . |
| 58-83619 | 5/1983 | Japan . |

OTHER PUBLICATIONS

*Chemische Berichte,* vol. 110, pp. 3664–3671.
*Chemistry of Organic Compounds,* pp. 169–173 & 204–205.
*Chemical Abstracts,* vol. 92, 33657u.

*Primary Examiner*—Donald B. Moyer
*Assistant Examiner*—Julie K. Parker
*Attorney, Agent, or Firm*—Oblon, Spivak, McClelland, Maier & Neustadt

[57] ABSTRACT

Disclosed herein are dialkanoyloxybenzylidene dialkanoate represented by the formula

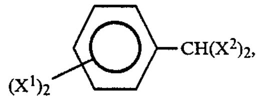

wherein $X^1$ and $X^2$ represent respectively alkanoyloxy group and a pharmaceutical composition in dosage unit form which comprises a dosage effective for the treatment of inflammatory disease of the dialkanoyloxybenzylidene dialkanoate as an active ingredient thereof.

4 Claims, 13 Drawing Sheets

DIALKANOYLOXYBENZYLIDENE DIALKANOATE

This is a division of application Ser. No. 06/681,289, filed Dec. 13, 1984 now U.S. Pat. No. 4,758,591.

BACKGROUND OF THE INVENTION

The present invention relates to a novel dialkanoyloxybenzeylidene dialkanoate represented by the formula (I):

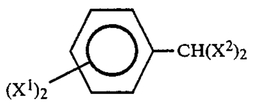
(I)

wherein $x^1$ and $x^2$ represent respectively alkanoyloxy group, and a pharmaceutical composition in dosage unit form which comprises a dosage effective for the treatment of inflammatory disease of a compound represented by the formula (I) and a pharmaceutially acceptable carrier.

Dihydroxybenzaldehyde has recently attracted attention as an antitumour agent (refer to Japanese Patent Application Laying-Open No. 55-51018(1980)) and as an anti-inflammatory agent (refer to Japanese Patent Application Laying-Open No. 58-83619(1983)).

However, although dihydroxybenzaldehyde shows an excellent pharmacological activity in suppressing platelet aggregation and migration of leukocytes at a relatively low concentration in vitro, owing to the rapid metabolism thereof in the living body, it is necessary to administer a large amount thereof for a long time period for obtaining the effective effects of such pharmacological activity in vivo, and there are difficulties in administering thereof due to the stimulus action and the oxidizability of the aldehyde moiety thereof.

As a result of the present inventors' studies for developing a pharmaceutical agent which exhibits an effective pharmacological activity when administered to a living body even at a small dose rate while scarcely showing side effects, the present inventors have found the compound synthesized by the reaction, for instance, between a dihydroxybenzaldehyde and an alkanoic acid anhydride, which is represented by the formula (I):

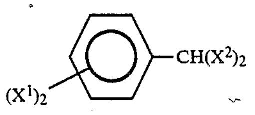
(I)

wherein $x^1$ and $x^2$ represent respectively alkanoyloxy group, and exhibits an effective pharmacological activity while scarcely showing side effects.

In the formula (I), the two $x^1$ may occupy any of the following positions in the benzene ring thereof.

(2,3), (2,4), (2,5), (2,6), (3,4) and (3,5).

The alkyl group of the alkanoyloxy group represented by $x^1$ and $x^2$, respectively is a straight-chain or branched-chain alkyl group of from 1 to 18 carbon atoms, and $x^1$ and $x^2$ are independently represented by the formulae,

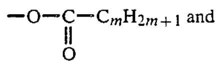 and 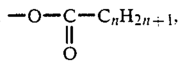, respectively.

SUMMARY OF THE INVENTION

In a first aspect of the present invention, there is provided a dialkanoyloxybenzylidene dialkanoate represented by the formula (I):

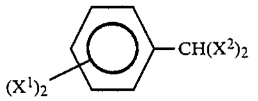
(I)

wherein $x^1$ and $x^2$ represent respectively the same or different alkanoyloxy group.

In a second aspect of the present invention, there is provided a process for producing a dialkanoyloxy-benzylidene dialkanoate represented by the formula (I):

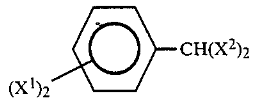
(I)

wherein $x^1$ and $x^2$ represent respectively alkanoyloxy group, which comprises reacting a dihydroxybenzaldehyde with an alkanoic acid anhydride.

In a third aspect of the present invention, there is provided a pharmaceutical composition in dosage unit form which comprises a dosage effective for the treatment of inflammatory disease of a dialkanoyloxybenzylidene dialkanoate represented by the formula (I):

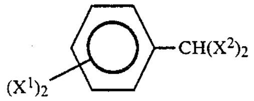
(I)

wherein $x^1$ and $x^2$ represent respectively the same or different alkanoyloxy group and a pharmaceutically acceptable carrier.

In a fourth aspect of the present invention, there is provided a method for the treatment of inflammatory disease, which comprises administering to a patient suffering therefrom a pharmaceutically effective amount of a dialkanoyloxybenzylidene dialkanoate represented by the formula (I):

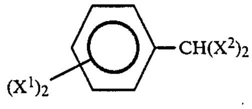
(I)

wherein $x^1$ and $x^2$ represent respectively alkanoyloxy group.

BRIEF EXPLANATION OF DRAWINGS

Of the attached drawing.

DETAILED DESCRIPTION OF THE INVENTION

Figure 1:
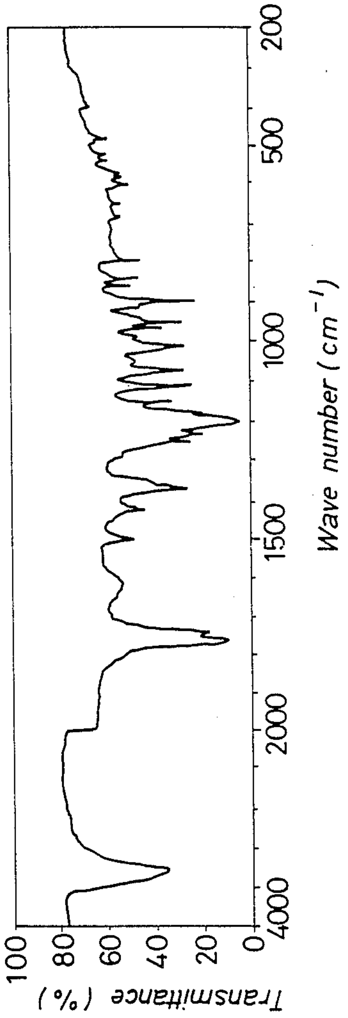
FIGS. 1, 3, 5 and 7 to 19 are the infrared absorption spectra of the present substances Nos. 1, 2, 3 and 4 to 16 according to the present invention, respectively.

The novel dialkanoyloxybenzylidene dialkanoate represented by the formula (I) according to the present invention (hereinafter referred to as the present substance), the process for producing thereof and the pharmacological composition having an anti-inflammatory activity comprising the present substance or containing the present substance as the active ingredient thereof are explained as follows.

Although the present substance can be synthesized by reacting an alkanoic acid anhydride with a dihydroxybenzaldehyde while heating a mixture of the two reactants in the presence of a strong alkali such as potassium hydroxide, sodium hydroxide and sodium acetate, the present substance can be profitably synthesized in a high yield when the alkanoic acid anhydride (III) is reacted with a dihydroxybenzaldehyde (II) in the presence of a strong acid such as sulfuric acid, hydrochloric acid and nitric acid, as is shown by the following reaction formula.

(1) In the case where $X^1$ and $X^2$ are the same.

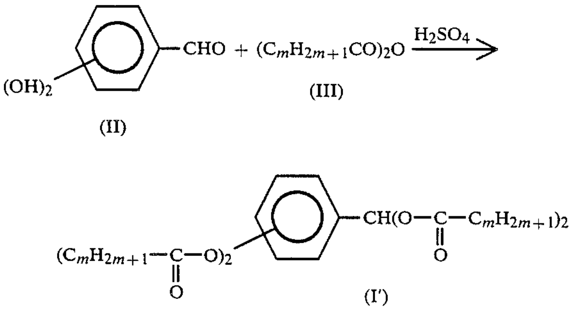

(II) (III) (I')

wherein the formula (I') represents the present substance in which $x^1$ and $x^2$ are the same and represented by

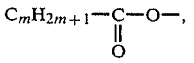

wherein m is an integer of 1 to 18.

Namely, to one mole of 2,3-; 2,4-; 2,5-; 2,6-; 3-4- or 3,5-dihydroxybenzaldehyde represented by the formula (II), more than 3 moles of the alkanoic acid anhydride represented by the formula (III) wherein m is an integer of from 1 to 18 are added, and after melting the anhydride at a temperature higher than the melting point of the anhydride and in a range of from room temperature to 100° C., a catalytic amount of a strong acid such as concentrated sulfuric acid, hydrochloric acid and nitric acid is rapidly added to the mixture while stirring thereof. Then, the reaction exothermically proceeds to obtain a homogeneous reaction mixture as a solution. The reaction completes within a time period of from one min to 5 hours, preferably from 2 min to one hour.

(2) In the case where $x^1$ and $x^2$ are different from each other, for instance, $x^1$ represents

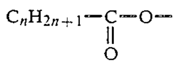

wherein n is an integer of 1 to 18, $x^2$ represents

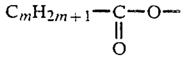 and n ≠ m, a derivative represented by the formula:

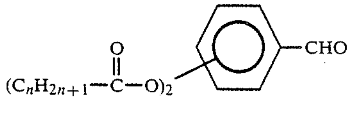

is reacted with an alkanoic acid anhydride represented by the formula $(C_mH_{2m+1}CO)_2O$.

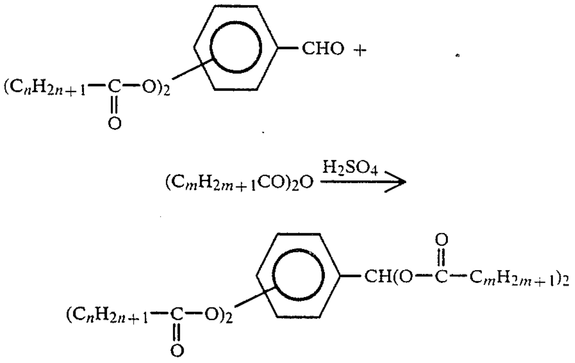

From the thus obtained reaction mixture, the present substance represented by the formula (I') can be isolated by one of known methods such as recrystallization, extraction and removal of the by-produced alkanoic acid by extraction, evaporation of the un-reacted anhydride of the alkanoic acid or column-chromatography.

The above-mentioned synthetic process only shows one embodiment for obtaining the present substance and accordingly, the process for production of the present substance should not be limited to the above-mentioned process.

Each of the present substances showed an activity of suppressing the migration of leukocytes, an activity of inhibiting the proliferation of granuloma and an activity of suppressing adjuvant arthritis as the results of in vivo tests. In addition, each of the present substances is less toxic than the known substances such as dihydroxybenzaldehyde and is effective at a smaller dose rate than that of the known substances such as dihydroxybenzaldehyde. Accordingly, each of the present substances has a pharmacological activity as an anti-inflammatory agent.

Namely, it is an ordinary anti-inflammatory agent, an anti-rheumatic agent against chronic arthritic rheumatism and an agent for treating auto-immune diseases such as glomerular nephritis and systemic lupus erythematodes.

The mammalian toxicity and pharmacological properties of the present substances are explained as follows by the following representative compounds of the present substances. The other compounds are also useful as the anti-inflammatory agent although some difference are seen among the activities thereof.

3,4-diacetoxybenzylidene diacetate, hereinafter referred to as the present substance No. 1, 2,3-diacetoxybenzylidene diacetate, hereinafter referred to as the present substance No. 2, 2,5-diacetoxybenzylidene diacetate, hereinafter referred to as the present substance No. 3, 3,4-dipropionyloxybenzylidene dipropionate, hereinafter referred to as the present substance No. 4, 3,4-di-n-dodecanoyloxybenzylidene di-n-dodecanoate, hereinafter referred to as the present substance No. 5, 3,4-di-n-octadecanoyloxybenzylidene di-n-octadecanoate, hereinafter referred to as the present substance No. 8 and 2,5-di-n-octadecanoyloxybenzylidene di-n-octadecanoate, hereinafter referred to as the present substance No. 10.

(1) Acute Mammalian Toxicity

After dispersing each of the present substances Nos. 1, 4, 5, 8 and 10 in an aqueous 0.2% solution of carboxymethylcellulose, the aqueous dispersion was orally administered to each of male Jcl-ICR mice. As a result, $LD_{50}$ (acute, oral) of each of the tested substances was larger than 4,000 mg/kg. $LD_{50}$ (acute, oral) of the present substances Nos. 2 and 3 to male Jcl-ICR mice was larger than 2,000 mg/kg.

On the other hand, $LD_{50}$ (acute, oral) of 3,4-dihydroxybenzaldehyde to male Jcl-ICR mice was 1503 mg/kg and accordingly, at least the above-mentioned present substances were found to be extremely low in acute mammalian toxicity.

(2) Activity in Suppressing the Migration of Leukocytes

While using groups of male Donryu rate (six rats per group) and following the carboxymethylcellulose-pouch method (refer to Ishikawa et al. Yakugaku Zasshi (Journal of the Pharmaceutical Society of Japan, 88, 1472, 1968), the extent of inhibition of migration of polymorphonuclear leuckocytes to the site of inflammation by the present substance was examined. The specimen (the present substance) was dispersed in an aqueous 0.2% solution of carboxymethylcellulose and the dispersion was administered to each rat at a predetermined dose rate, and only the aqueous 0.2% solution of carboxymethylcellulose was administered to each rat of control group. Test was carried out by injecting the aqueous 0.2% solution of carboxymethylcellulose into the pouch formed in the body of the rat and after 6 hours of the injection, the number of polymorphonuclear leukocytes in the exudate into the pouch was counted. The results are shown in Table 1, and as are seen in Table 1, it was confirmed that the present substance significantly suppressed the migration of polymorphonuclear leukocytes (PMN) to the site of inflammation.

TABLE 1

| Group of test animals | Dose rate (mg/kg) | Number of PMN in exudate(1) (mean ± SE) | Rate of suppression of migration of PMN (%) |
|---|---|---|---|
| Control | — | 10.2 ± 0.64 | — |
| Group administered with Present Substance No. 1 | 5 | 6.0 ± 1.00** | 41.2 |
| | 10 | 5.3 ± 0.47*** | 48.0 |
| | 50 | 4.9 ± 0.48*** | 51.9 |
| Control | — | 10.92 ± 0.81 | — |
| Present Substance No. 4 | 50 | 5.08 ± 0.28*** | 53.5 |
| Present Substance No. 5 | 50 | 4.85 ± 0.43*** | 55.6 |
| Present Substance No. 8 | 50 | 4.76 ± 0.54*** | 56.4 |
| Present substance No. 10 | 50 | 6.23 ± 0.15*** | 42.9 |
| Administered with Prednisolone | 5 | 6.83 ± 0.27*** | 37.5 |
| Administered with Indomethacin | 5 | 7.02 ± 0.64** | 35.7 |
| Administered with 3,4-dihydroxybenzaldehyde | 50 | 7.92 ± 0.36* | 27.5 |

Notes:
(1)(number of PMN/$mm^3$ of the exudate) × 10
*$P < 0.05$
**$P < 0.01$
***$P < 0.005$ (3) Activity in Suppressing the Proliferation of Granuloma While using groups of male Donryu rats in the fifth week after birth (5 rats per group), the activity of the present substance is suppressing the proliferation of granuloma was tested by the method of Fujimura (refer to Oyoyakuri (Pharmacometrics), 19(3) 329, 1980).

After soaking sheets of filter paper of 13 mm in diameter and 28 mg in weight into an aqueous 2% solution of carboxymethylcellulose containing both dihydroxystreptomycin and penicillin, each of $10^6$ unit at the respective concentration of 0.1 mg/ml, each of the thus treated sheets was buried subcutaneously into the back of each rat under anesthesia by ether. Each specimen (the present substances) to be tested was dispersed in an aqueous 0.3% solution of carboxymethylcellulose and the dispersion was administered orally to the thus treated rat after the rat had been awaken from the anesthesia once a day for 10 days. After 11 days of the treatment, granuloma formed in the rat was removed, dried for 24 hours at 70° C. and weighed. To the rats of control group, only the aqueous 0.3% solution of carboxymethylcellulose was orally administered once a day for 10 days, both results being shown in Table 2.

As are seen in Table 2, each of the tested present substances significantly suppressed the proliferation of granulating tissue formed.

TABLE 2

| Group of test animals | Dose rate (mg/kg/day) | Granuloma: Dried weight(1) (mg) | Granuloma: Rate of suppression (%) |
|---|---|---|---|
| Control | — | 88.1 ± 5.0 | — |
| Present Substance No. 1 | 5 | 50.4 ± 8.4** | 42.8 |
| | 10 | 39.4 ± 3.0*** | 55.3 |
| | 50 | 34.0 ± 4.2*** | 61.4 |
| Control | — | 109.4 ± 7.5 | |
| Present Substance No. 4 | 50 | 42.4 ± 5.7*** | 61.2 |
| Present Substance No. 5 | 50 | 39.1 ± 3.4*** | 64.7 |

TABLE 2-continued

| Group of test animals | Dose rate (mg/kg/day) | Granuloma Dried weight[1] (mg) | Rate of suppression (%) |
|---|---|---|---|
| Present Substance No. 8 | 50 | 36.2 ± 2.6*** | 66.9 |
| Present Substance No. 10 | 50 | 57.0 ± 6.7*** | 47.9 |
| Administered with Indomethacin | 3 | 66.3 ± 8.4** | 39.4 |
| Administered with Prednisolone | 3 | 63.2 ± 8.6** | 42.2 |
| Administered with 3,4-dihydroxybenzaldehyde | 50 | 70.5 ± 9.7* | 35.6 |

Notes:
[1]mean value ± standard error
*P < 0.05
**P < 0.01
***P < 0.005

(4) Activity in Suppressing Adjuvant Arthritis

While using groups of female Jcl-SD rats in the 8th week after birth (6 rats per group), the activity of the present substance is suppressing the adjuvant arthritis was tested by the method of Fujihira et al. (refer to Oyoyakuri (Pharmacometrics), 5(2), 169, 1971).

Namely, Freund's complete adjuvant was implanted to the tail of each rat under anesthesia by ether in an amount of 0.6 mg dissolved in 0.1 ml of mineral oil, and after 2 weeks of the implantation, each specimen (the present substances) to be tested was orally administered once a day for 20 days, and the state of the rat was observed.

As the results of the above-mentioned test, each of the present substances tested, namely, Nos. 1, 2, 3, 4, 5, 8 and 10 showed an excellent treating effect on the adjuvant arthritis caused by the implanted Freund's complete adjuvant. On the other hand, in the rats administered with prednisolone, the increase of the body weight was significantly suppressed, and on the autopsy thereof, a significant atrophy of the thymus thereof was observed. In the rats administered with each of the present substance, suppression of increase of body weight and atrophy of the thymus were not observed. The findings confirm that the present substance has scarcely the side effects.

Accordingly, the present substance is effective as an agent for treating chronic inflammatory diseases such as rheumatism, etc.

As are seen in the above-mentioned test results, it can be recognized that the present substance has the excellent activities in suppressing the proliferation of granuloma, in suppressing the adjuvant arthritis and in suppressing the migration of leukocytes and is extremely low in acute mammalian toxicity.

Accordingly, the present substance can be used in the extremely important uses as an anti-inflammatory agent, an anti-chronic arthritic rheumatism and an agent for treating autoimmune diseases such as systemic lupus erythematodes and glomerular nephritis.

The present substance is possibly administered orally, intraintestinally or in the form of injection in one of the various forms of pharmaceutical formulation (so-called pharmaceutical composition) after being combined with pharmaceutically acceptable carrier(s) and/or adjuvant(s). More than two of the present substances may be used in combination or after being mixed together, and the present substance may be used after being combined with any other active ingredient for pharmaceutical use.

Since the present substance can be administered orally and parenterally, it can take any optional form of pharmaceutical compositions suitable for the route of administration. In addition, the present substance may be offered in the unit dose form, and as far as the pharmaceutical composition contains an effective amount of the present substance, the composition can take the various forms such as powder, granule, tablet, sugar-coated tablet, capsule, suppository, suspension, solution, emulsion, ampoule and injection.

Accordingly, it should be recognized that the pharmaceutical composition comprising the present substance can be formulated by application of any known means for formulation of a pharmacologically active agent.

In addition, the content of the present substance as an active ingredient in the above-mentioned pharmaceutical composition can be adjusted in a broad range of from 0.01 to 100% by weight, preferably in a range of from 0.1 to 70% by weight.

As has been stated, although the pharmaceutical composition comprising the present substance is orally or parenterally administered to human or mammals, the oral administration including sublingual administration is particularly preferable.

The parenteral administration includes subcutaneous-, intramuscular- and intravenous injection and instillation.

Since the dose rate of the present substance depends on the species, the sex, the age, the individual difference and the state of the disease of the patient to be administered therewith, there may be cases where an amount outside the following range is administered, however, in the cases where human being is the object of administration, the oral daily dose rate of one of the present substances is in a range of from 0.1 to 500 mg/kg body weight, preferably in a range of from 0.5 to 200 mg/kg body weight, more preferably in the range of from 3 to 100 mg/kg body weight, and the parenteral daily dose rate is is a range of from 0.1 to 200 mg/kg body weight, preferably in a range of from 0.1 to 100 mg/kg body weight, more preferably in the range of from 1.5 to 50 mg/kg body weight. The above-mentioned daily amount is divided equally into 1 to 4 portions, and the thus divided portion is administered at a time (one to four times per day).

The present invention will be explained more in detail while referring to the following non-limitative examples.

EXAMPLE 1

Synthesis of 3,4-diacetoxybenzylidene diacetate (the present substance No. 1)

After introducing 30 g of protocatechualdehyde (3,4-dihydroxybenzaldehyde) and 92.4 g of acetic anhydride into a 200 ml-flask and adding one drop of concentrated sulfuric acid to the content of the flask, the flask was shaken to rapidly induce a beginning of an exothermic reaction, thereby obtaining a uniform liquid reaction mixture of red in colour. After shaking the flask for 3 min, the liquid reaction mixture was poured into 500 ml of water to form a colourless, powdery crude product as a precipitate. The amount of the crude product after collecting the precipitate by filtration and drying thereof was 68.0 g (the yield: 96.6%). By subjecting the dried, crude product to recrystallization from a 2:1 mixed solvent of ethanol and ethyl acetate, 59.9 g of colourless prisms (the yield: 85.0%) were obtained as the product of the process according to the present invention, the physical properties thereof being shown as follows:

(1) Melting point: 129.0 to 130.0° C. (by capillary method)

(2) Elementary analytical data:

| | C (%) | H (%) |
|---|---|---|
| Found | 55.70 | 4.90 |
| Calcd. as $C_{15}H_{16}O_8$ | 55.56 | 4.97 |

(3) Infrared absorption spectrum (by KBr-tablet method) The spectrum is shown in FIG. 1.

Figure 2:
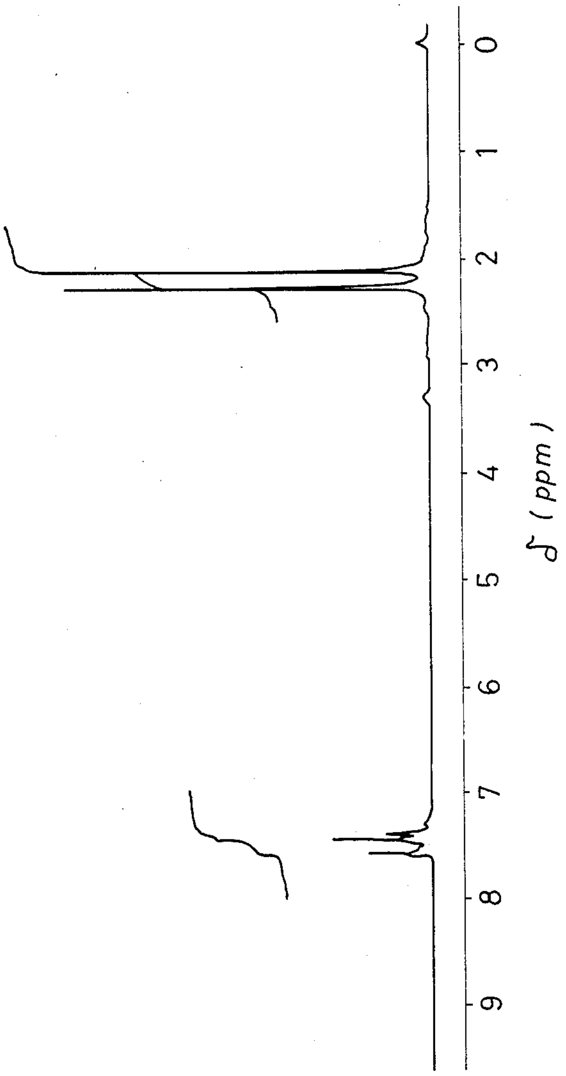
FIGS. 2, 4 and 6 are the nuclear magnetic resonance spectra of the present substances Nos. 1, 2 and 3, respectively.

(4) Nuclear magnetic resonance spectrum of $^1H$: The spectrum is shown in FIG. 2 with the following peaks: δ(DMSO—$d_6$) ppm, 2.12(s): [Ar—C(OCOCH$_3$)$_2$, (6H)], 2.28(s): [Ar—OCOCH$_3$, (6H)], 7.37 to 7.42(m): [Ar—H, (3H)], O—
7.55(s): [Ar—CH , (1H)]
O—

EXAMPLE 2

Synthesis of 2,3-diacetoxybenzylidene diacetate (the present substance No. 2)

In the same procedures as in Example 1 except for using 2,3-dihydroxybenzaldehyde instead of protocatechualdehyde in Example 1, the crude product of the objective substance was obtained, and by recrystallizing thereof from ethyl acetate, a colourless powdery substance was obtained as the present substance No. 2 in a yield of 78.7%. The physical properties of the product are shown as follows.

(1) Melting point: 108.5 to 109.5° C. (by capillary method)

(2) Elementary analytical data:

| | C (%) | H (%) |
|---|---|---|
| Found | 55.70 | 4.80 |
| Calcd. as $C_{15}H_{16}O_8$ | 55.56 | 4.97 |

Figure 3:
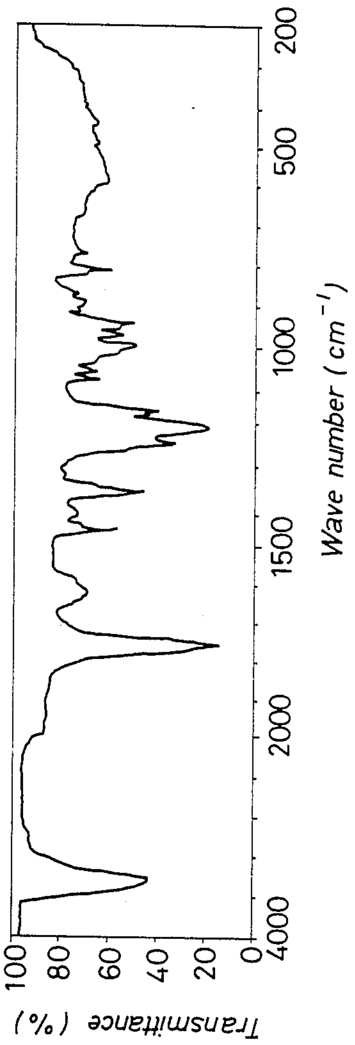

(3) Infrared absorption spectrum (by KBr-tablet method): The spectrum is shown in FIG. 3.

Figure 4:
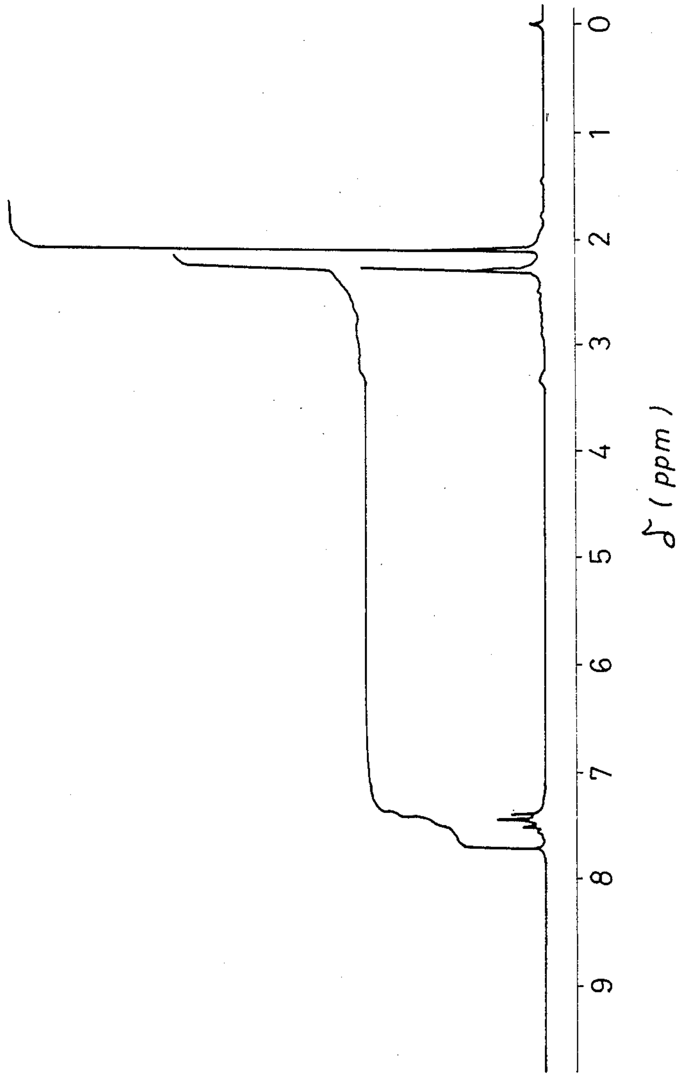

(4) Nuclear magnetic resonance spectrum of $^1H$: The spectrum is shown in FIG. 4 with the following peaks. δ(DMSO—$d_6$)

2.09(s): [Ar—C(OCOCH$_3$)$_2$, (6H)], 2.27(s), 2.30(s): [Ar—OCOCH$_3$, (6H)], 7.37 to 7.59(m): [Ar—H, (3H)],

O—
7.70(s): [Ar—CH , (1H)]
O—

EXAMPLE 3

Synthesis of 2,5-diacetoxybenzylidene diacetate (the present substance No. 3)

In the same procedures as in Example 1 except for using 2,5-dihydroxybenzaldehyde instead of protocatechualdehyde in Example 1, the crude product of the object substance was obtained, and by recrystallizing the crude product from ethyl acetate, colourless prism were obtained as the product according to the present invention in a yield of 81.3%. The physical properties of the thus recrystallized product are shown as follows.

(1) Melting point: 128.5 to 129.5° C. (by capillary method)

(2) Elementary analytical data:

| | C (%) | H (%) |
|---|---|---|
| Found | 55.70 | 4.90 |
| Calcd. as $C_{15}H_{16}O_8$ | 55.56 | 4.97 |

Figure 5:
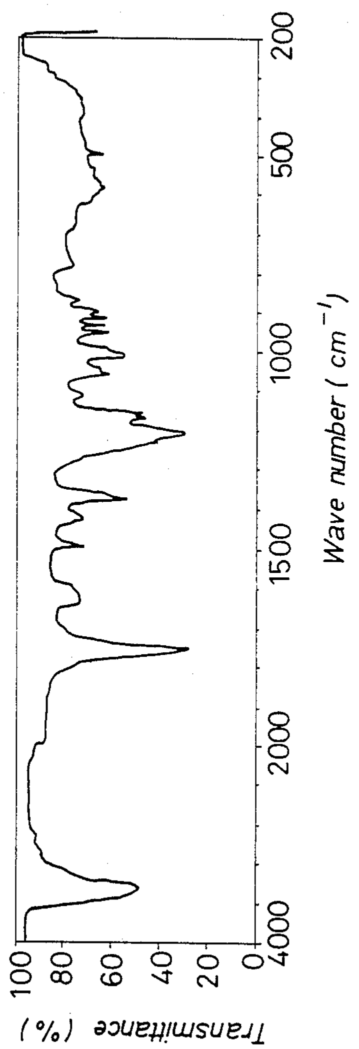

(3) Infrared absorption spectrum (by KBr-tablet method): The spectrum is shown in FIG. 5.

Figure 6:
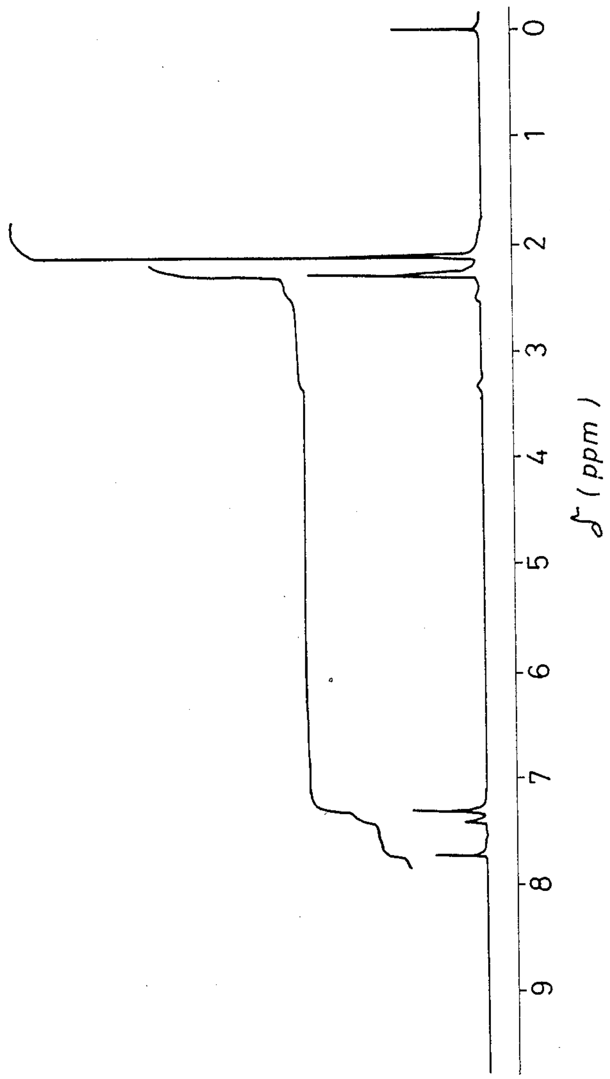

(4) Nuclear magnetic resonance spectrum of $^1H$: The spectrum is shown in FIG. 6 with the following peaks. δ(in DMSO—$d_6$), ppm 2.10(s): [Ar—C(OCOCH$_3$)$_2$, (6H)], 2.26(s), 2.28(s): [Ar—OCOCH$_3$, (6H)], 7.27 to 7.38(m): [Ar—H, (3H)], O—
7.70(s): [Ar—CH , (1H)]
O—

EXAMPLE 4

Synthesis of 3,4-dipropionyloxybenzylidene dipropionate (the present substance No. 4)

After introducing 20.0 g of protocatechualdehyde (3,4-dihydroxybenzaldehyde) and 76.3 g of propionic acid anhydride into a 200 ml-flask and adding one drop of concentrated sulfuric acid to the mixture in the flask, the flask was shaken to rapidly induce the beginning of an exothermic reaction, thereby obtaining a nearly uniform liquid reaction mixture of red in colour. After shaking the flask for 5 min, the liquid reaction mixture was poured into 300 g of water to obtain a crude powdery product of whitish yellow in colour. By recrystallizing the thus obtained crude product from a mixed solvent of methanol and water, 45.9 g of colourless prisms product were obtained in a yield of 83.2%, the physical properties thereof being shown as follows.

(1) Melting point: 64.0 to 65.0° C. (by capillary method)

(2) Elementary analytical data:

| | C (%) | H (%) |
|---|---|---|
| Found | 60.00 | 6.30 |
| Calcd. as $C_{19}H_{24}O_8$ | 59.99 | 6.36 |

Figure 7:
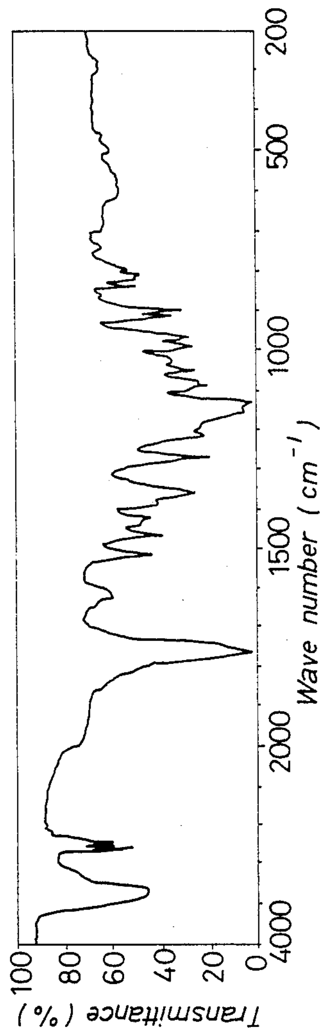

(3) Infrared absorption spectrum (by KBr-tablet method): The spectrum is shown in FIG. 7.

(4) Nuclear magnetic resonance spectrum of $^1H$: δ(in DMSO—$d_6$) ppm:

-continued

| |
|---|
| O<br>‖<br>0.97 to 1.20(m): [O—C—C—$CH_3$, (12H)], |
| 2.32 to 2.71(m): [—$OCOCH_2$—, (8H)], |
| 7.29 to 7.50(m): [Ar—H, (3H)], |
| O—<br>7.59(s): [Ar—CH , (1H)]<br>O— |

EXAMPLE 5

Synthesis of 3,4-didodecanoyloxybenzylidene didodecanoate (the present substance No. 5)

After introducing 11.4 g of protocatechualdehyde and 127.8 g of dodecanoic acid anhydride into a 500 ml-flask, the mixture was heated to 80° to 85° C. to obtain a heterogeneous solution consisting of solid protocatechualdehyde and liquefied dodecanoic acid anhydride. After adding one drop of concentrated sulfuric acid to the mixture, the thus formed mixture was shaken to rapidly induce an exothermic reaction, thereby obtaining a nearly homogeneous reaction mixture of reddish brown in colour. After heating the liquid reaction mixture for 40 min at 80° to 95° C., a mixed solvent of 500 ml of ethanol and 50 ml of ethyl acetate was added to the reaction mixture, and the thus formed mixture was cooled to room temperature and left for while to form scaly crystals of white in colour as a precipitate. After collecting the crystals by filtration, the crystals were dried to be 56.0 g of the white scaly product in a yield of 76.7%, the physical properties of the thus obtained white scaly crystals being shown as follows.

(1) Melting point: 52.0 to 53.0° C. (by capillary method)

(2) Elementary analytical data:

| | | C(%) | H(%) |
|---|---|---|---|
| Found | : | 74.80 | 11.20 |
| Calcd. as $C_{55}H_{96}O_8$ | : | 74.61 | 10.93 |

Figure 8:
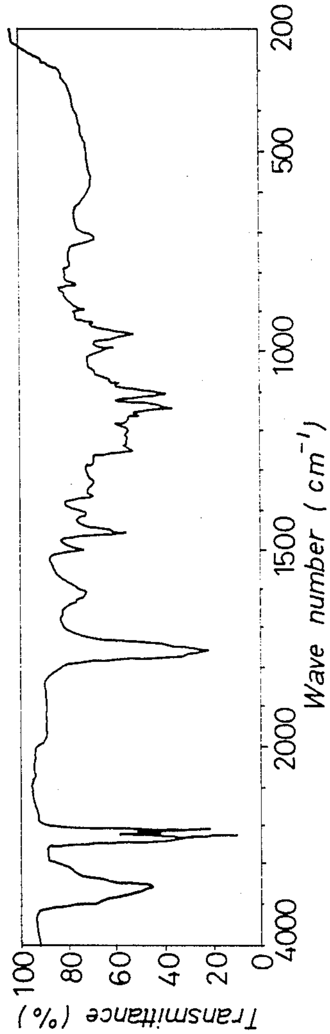

(3) Infrared absorption spectrum (by KBr-tablet method): The spectrum is shown in FIG. 8.

(4) Nuclear magnetic resonance spectrum of $^1H$: δ(in DMSO—d6) ppm:

0.79 to 0.98(m): [—C—$CH_3$, (12H)], 1.17 to 1.54(m): [—C—$CH_2$—C—, (72H)], 2.1 to 2.26(m): [Ar—$C(OCOCH_2R)_2$, (4H)], 2.46 to 2.66(m): [Ar—$OCOCH_2R$, (4H)],

O—
7.47 to 7.94(m): [Ar—H and Ar—CH , (4H)]
O—

EXAMPLE 6

Synthesis of 3,4-di-n-tetradecanoyloxybenzylidene di-n-tetradecanoate (the present substance No. 6)

In the same procedures as in Example 5 except for using n-tetradecanoic acid anhydride instead of dodecanoic acid anhydride in Example 5, crystals were obtained, and the crystals were recrystallized from a mixed solvent (5:1) of ethanol and ethyl acetate to obtain a powdery white product in a yield of 69.7%. The physical properties of the thus obtained product are shown as follows.

(1) Melting point: 63.5 to 64.5° C. (by capillary method)

(2) Elementary analytical data:

| | | C(%) | H(%) |
|---|---|---|---|
| Found | : | 76.00 | 11.60 |
| Calcd. as $C_{63}H_{112}O_8$ | : | 75.85 | 11.32 |

Figure 9:
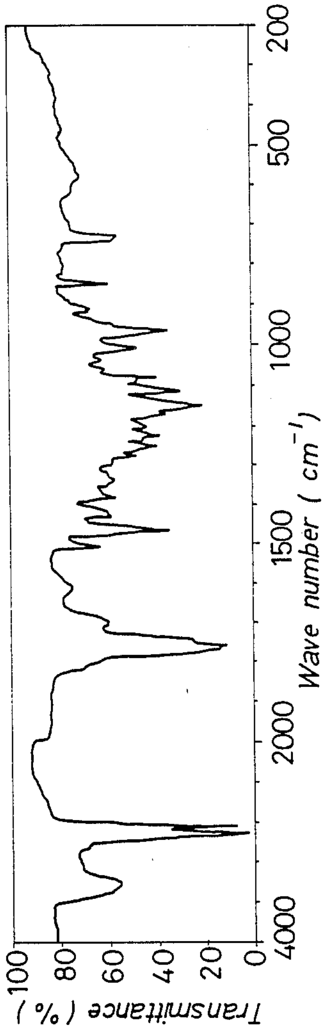

(3) Infrared absorption spectrum (by KBr-tablet method): The spectrum is shown in FIG. 9.

(4) Nuclear magnetic resonance spectrum of $^1H$: δ(in $CDCl_3$) ppm 0.87 to 0.93(m): [—C—$CH_3$, (12H)], 1.25 to 1.61(m): [—C—$CH_2$—C—, (88H)], 2.29 to 2.59(m): [—O—C—$CH_2$—, (8H)],
‖
O 7.14 to 7.42(m): [Ar—H, (3H)], O—
7.67(s): [Ar—CH , (1H)].
O—

EXAMPLE 7

Synthesis of 3,4-di-n-hexadecanoyloxybenzylidene di-n-hexadecanoate (the present substance No. 7)

In the same procedures as in Example 5 except for using n-hexadecanoic acid anhydride instead of dodecanoic acid anhydride in Example 5, crystals were obtained and by recrystallizing thereof from a mixed solvent (2:1) of ethanol and ethyl acetate, a powdery white product was obtained in a yield of 72.9%.

The physical properties of the thus obtained product are shown as follows.

(1) Melting point: 70.5 to 71.5° C. (by capillary method)

(2) Elementary analytical data:

| | | C(%) | H(%) |
|---|---|---|---|
| Found | : | 76.90 | 11.70 |
| Calcd. as $C_{71}H_{128}O_8$ | : | 76.84 | 11.63 |

Figure 10:
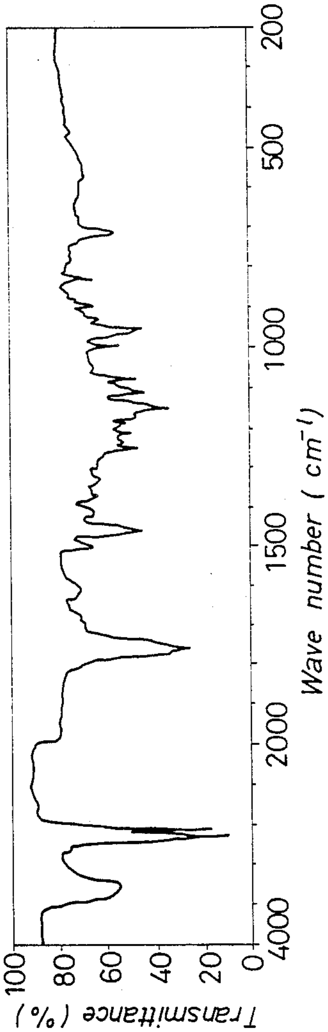

(3) Infrared absorption spectrum (by KBr-tablet method) The spectrum is shown in FIG. 10.

(4) Nuclear magnetic resonance spectrum of $^1H$: δ(in $CDCl_3$) ppm

-continued 0.81 to 0.94(m): [—C—$CH_3$, (12H)], 1.25 to 1.62(m): [—C—$CH_2$—C—, (104H)], 2.28 to 2.60(m): [—O—C—$CH_2$—, (8H)], 7.13 to 7.43(m): [Ar—H, (3H)], 7.67(s): [Ar—CH , (1H)]

EXAMPLE 8

Synthesis of 3,4-di-n-octadecanoyloxybenzylidene di-n-octadecanoate (the present substance No. 8)

In the same procedures as in Example 5 except for using n-octadecanoic acid anhydride instead of dodecanoic acid anhydride in Example 5, crystals were obtained and by recrystallizing the crystals from a mixed solvent (2:1) of ethanol and ethyl acetate, a powdery white product was obtained in a yield of 73.4%. The physical properties of the thus obtained product are shown as follows.

(1) Melting point: 77.0 to 78.0° C. (by capillary method)

(2) Elementary analytical data:

| | | C(%) | H(%) |
|---|---|---|---|
| Found | : | 77.40 | 12.10 |
| Calcd. as $C_{79}H_{144}O_8$ | : | 77.65 | 11.89 |

Figure 11:
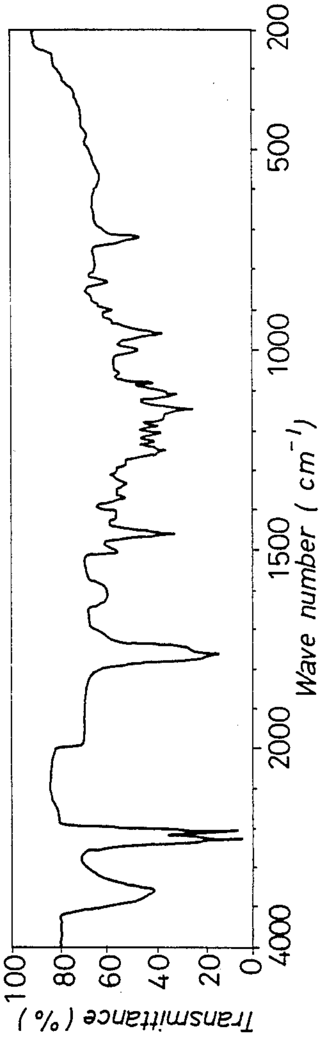

(3) Infrared absorption spectrum (by KBr-tablet method): The spectrum is shown in FIG. 11.

(4) Nuclear magnetic resonance spectrum of $^1H$: δ(in $CDCl_3$) ppm, 0.82 to 0.88(m): [—C—$CH_3$, (12H)], 1.25 to 1.61(m): [—C—$CH_2$—C—, (120H)], 2.28 to 2.60(m): [—O—C—$CH_2$—, (8H)], 7.15 to 7.44(m): [Ar—H, (3H)], 7.67(s): [Ar—CH , (1H)].

EXAMPLE 9

Synthesis of 2,5-di-n-dodecanoyloxybenzylidene di-n-dodecanoate (the present substance No. 9)

In the same procedures as in Example 5 except for using 2,5-dihydroxybenzaldehyde instead of protocatechualdehyde in Example 5, crystals were obtained, and by recrystallizing the crystals from a mixed solvent (2:1) of ethanol and ethyl acetate, a powdery white product was obtained in a yield of 76.9%. The physical properties of the thus obtained product are shown as follows.

(1) Melting point: 62.0 to 63.0° C. (by capillary method)

(2) Elementary analytical data:

| | | C(%) | H(%) |
|---|---|---|---|
| Found | : | 74.50 | 11.00 |
| Calcd. as $C_{55}H_{96}O_8$ | : | 74.61 | 10.93 |

Figure 12:
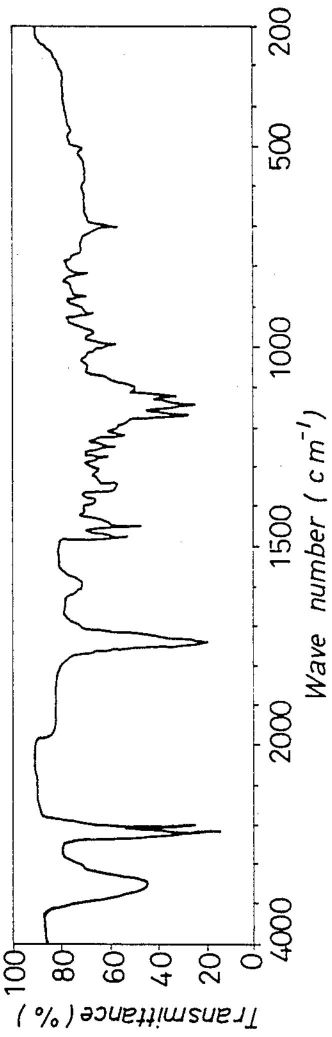

(3) Infrared absorption spectrum (by KBr-tablet method): The spectrum is shown in FIG. 12.

(4) Nuclear magnetic resonance spectrum: δ(in $CDCl_3$) ppm, 0.82 to 0.87(m): [—C—$CH_3$, (12H)], 1.25 to 1.56(m): [—C—$CH_2$—C—, (72H)], 2.25 to 2.67(m): [—O—C—$CH_2$—, (8H)], 7.11 to 7.33(m): [Ar—H, (3H)], 7.85(s): [Ar—CH , (1H)]

EXAMPLE 10

Synthesis of 2,5-di-n-octadecanoyloxybenzylidene di-n-octadecanoate (the present substance No. 10)

In the same procedures as in Example 5 except for using 2,5-dihydroxybenzaldehyde instead of protocatechualdehyde in Example 5 and further using n-octadecanoic acid anhydride instead of dodecanoic acid anhydride in Example 5, crystals were obtained and by recrystallizing the thus obtained crystals from a mixed solvent (2:1) of ethanol and ethyl acetate, a white powdery product was obtained in a yield of 82.8%. The physical properties of the thus obtained product are shown as follows.

(1) Melting point: 84.0 to 85.0° C. (by capillary method)

(2) Elementary analytical data:

| | | C(%) | H(%) |
|---|---|---|---|
| Found | : | 77.40 | 12.00 |
| Calcd. as $C_{79}H_{144}O_8$ | : | 77.65 | 11.89 |

Figure 13:
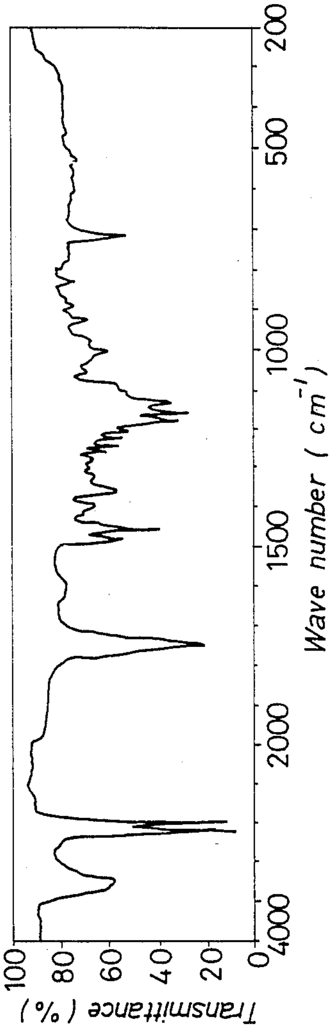

(3) Infrared absorption spectrum (by KBr-tablet method): The spectrum is shown in FIG. 13.

(4) Nuclear magnetic rêsonance spectrum of $^1H$: δ(in $CDCl_3$), ppm,

-continued 0.81 to 0.92(m): [—C—$CH_3$, (12H)], 1.25 to 1.66(m): [—C—$CH_2$—C—, (120H)], 2.24 to 2.59(m): [—O—C(=O)—$CH_2$—, (8H)], 7.11 to 7.33(m): [Ar—H, (3H)], 7.85(s): [Ar—CH(O—)(O—), (1H)].

EXAMPLE 11

Synthesis of 2,3-di-n-octadecanoyloxybenzylidene di-n-octadecanoate (the present substance No. 11)

In the same procedures as in Example 5 except for using 2,3-dihydroxybenzaldehyde instead of protocatechualdehyde in Example 5, and further using n-octadecanoic acid anhydride instead of dodecanoic acid anhydride in Example 5, crystals were obtained, and by recrystallizing the thus obtained crude crystals from a mixed solvent (5:1) of ethanol and ethyl acetate, a white powdery product was obtained in a yield of 90.0%. The physical properties of the thus obtained product, the present substance No. 11, are shown as follows.

(1) Melting point: 64.0 to 65.0° C. (by capillary method)

(2) Elementary analytical data:

| | | C(%) | H(%) |
|---|---|---|---|
| Found | : | 77.80 | 12.10 |
| Calcd. as $C_{79}H_{144}O_8$ | : | 77.65 | 11.89 |

Figure 14:
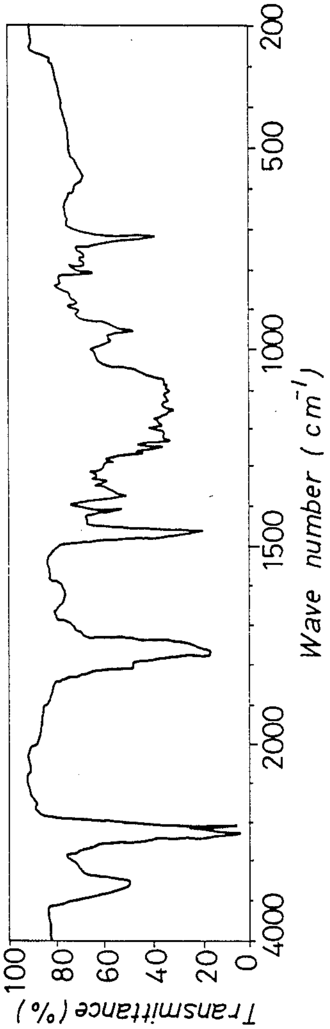

(3) Infrared absorption spectrum (by KBr-tablet method): The spectrum is shown in FIG. 14.

(4) Nuclear magnetic resonance spectrum of $^1H$: δ(in $CDCl_3$), ppm 0.82 to 0.93(m): [—C—$CH_3$, (12H)], 1.26 to 1.62(m): [—C—$CH_2$—C—, (120H)], 2.24 to 2.67(m): [—O—C(=O)—$CH_2$—, (8H)], 7.24 to 7.53(m): [Ar—H, (3H)], 7.86(s): [Ar—CH(O—)(O—), (1H)].

EXAMPLE 12

Synthesis of 3,4-di-n-butyryloxybenzylidene di-n-butyrate (the present substance No. 12)

In a 300 ml-flask, 10 g of protocatechualdehyde and 43.3 g of butyric acid anhydride were introduced, and after adding one drop of concentrated sulfuric acid to the resultant mixture, the flask was shaken for 10 min at room temperature to obtain a liquid reaction mixture of reddish brown in colour. After adding 200 ml of ethyl acetate to the liquid reaction mixture, the system was extracted five times with each 80 ml of an aqueous 1N solution of sodium hydrogen carbonate for the removal of butyric acid contained in the liquid reaction mixture. After washing the organic layer with an aqueous saturated solution of sodium chloride, the thus washed organic layer was dried on anhydrous sodium sulfate and decolorized by treatment with activated carbon and subjected to evaporation under a reduced pressure to remove the solvent. The residue was subjected further to distillation under a reduced pressure by heating for the removal of still remaining butyric acid anhydride thereby obtaining a pale yellow oily product in a yield of 97.4%. The physical properties of the thus obtained oily product are shown as follows.

(1) Elementary analytical data:

| | C (%) | H (%) |
|---|---|---|
| Found | 63.10 | 7.40 |
| Calcd. as $C_{23}H_{32}O_8$ | 63.29 | 7.39 |

Figure 15:
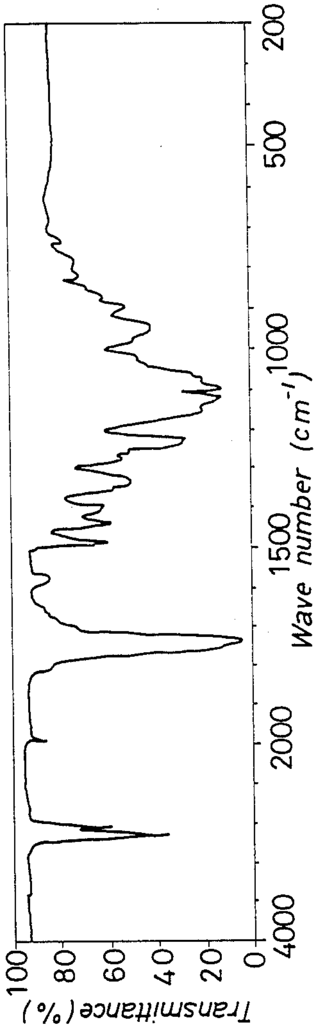

(2) Infrared absorption spectrum (by NaCl plate method): The spectrum is shown in FIG. 15.

(3) Nuclear magnetic resonance spectrum δ(in $CDCl_3$), ppm, 0.87 to 1.11(m): [—C—$CH_3$, (12H)], 1.48 to 1.96(m): [—C—$CH_2$—C—, (8H)], 2.27 to 2.60(m): [—O—C(=O)—$CH_2$—, (8H)], 7.15 to 7.46(m): [Ar—H, (3H)], 7.69(s): [Ar—CH(O—)(O—), (1H)].

EXAMPLE 13

Synthesis of 2,5-di-n-butyryloxybenzylidene di-n-butyrate (the present substance No. 13)

In the same procedures as in Example 12 except for using 2,5-dihydroxybenzaldehyde instead of protocatechualdehyde in Example 12, a pale yellow oily product, the present substance No. 13 was obtained in a yield of 97.5%. The physical properties of the product are shown as follows.

(1) Elementary analytical data:

| | C (%) | H (%) |
|---|---|---|
| Found | 63.50 | 7.10 |
| Calcd. as $C_{23}H_{32}O_8$ | 63.29 | 7.39 |

Figure 16:
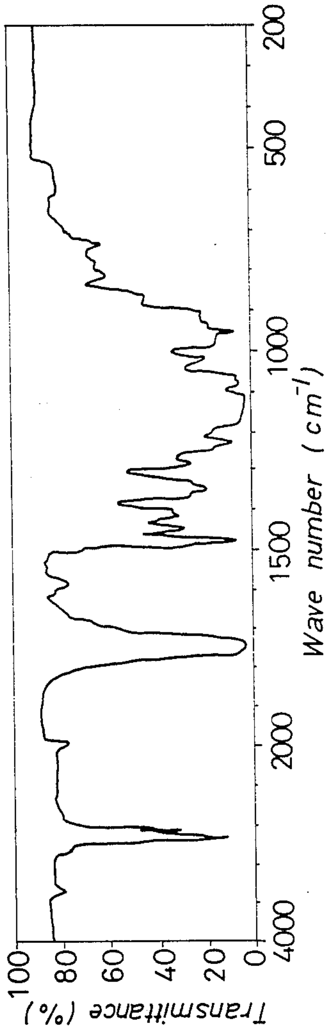

(2) Infrared absorption spectrum (by NaCl plate method): The spectrum is shown in FIG. 16.

(3) Nuclear magnetic resonance spectrum of $^1H$: δ(in $CDCl_3$), ppm, 0.86 to 1.11(m): [—$\overset{|}{\underset{|}{C}}$—$CH_3$, (12H)], 1.47 to 1.97(m): [—$\overset{|}{\underset{|}{C}}$—$CH_2$—$\overset{|}{\underset{|}{C}}$—, (8H)], 2.25 to 2.67(m): [—O—$\underset{\overset{\|}{O}}{C}$—$CH_2$—, (8H)], 7.12 to 7.37(m): [Ar—H, (3H)], 7.87(s): [Ar—CH$\overset{\diagup O—}{\diagdown O—}$, (1H)].

EXAMPLE 14

Synthesis of 2,3-di-n-butyryloxybenzylidene di-n-butyrate (the present substance No. 14)

In the same procedures as in Example 12 except for using 2,3-dihydroxybenzaldehyde instead of protocatechualdehyde in Example 12, a pale yellow oily product, the present substance No. 14, was obtained in a yield of 98.4%. The physical properties of the thus obtained oily product are shown as follows.

(1) Elementary analytical data:

| | C (%) | H (%) |
|---|---|---|
| Found | 63.50 | 7.20 |
| Calcd. as $C_{23}H_{32}O_8$ | 63.29 | 7.39 |

Figure 17:
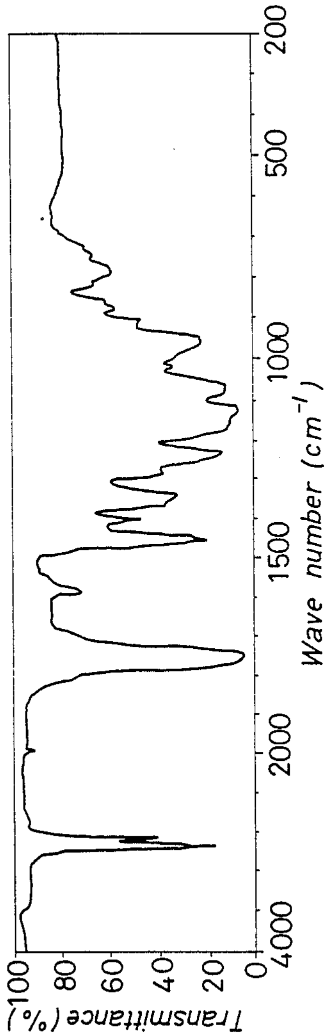

(2) Infrared absorption spectrum (by NaCl plate method): The spectrum is shown in FIG. 17.

(3) Nuclear magnetic resonance spectrum of $^1H$: δ(in $CDCl_3$), ppm, 0.85 to 1.12(m): [—$\overset{|}{\underset{|}{C}}$—$CH_3$, (12H)], 1.46 to 1.96(m): [—$\overset{|}{\underset{|}{C}}$—$CH_2$—$\overset{|}{\underset{|}{C}}$—, (8H)], 2.23 to 2.67(m): [—O—$\underset{\overset{\|}{O}}{C}$—$CH_2$—, (8H)], 7.12 to 7.54(m): [Ar—H, (3H)], 7.87(s): [Ar—CH$\overset{\diagup O—}{\diagdown O—}$, (1H)].

EXAMPLE 15

Synthesis of 3,4-diacetoxybenzylidene dioctadecanoate (the present substance No. 15)

In 100 ml-flask, 11.11 g of 3,4-diacetoxybenzaldehyde and 27.55 g of stearic acid anhydride were introduced, and after heating the mixture at 80° to 85° C. to obtain a homogenous solution, one drop of concentrated sulfuric acid was added to the solution and the mixture was reacted at 80° to 85° C. for 20 min under agitation. After the reaction was over, the reaction mixture was dissolved in 150 ml of ethyl acetate while heating the reaction mixture. The white powdery crystals were separated from the reaction mixture after leaving the reaction mixture to cool, collected by filtration and dried to obtain 27.64 g of a product in a yield of 71.50%.

The thus obtained product showed the following properties.

(1) Melting point: 75.0 to 76.0° C. (by capillary method)

(2) Elementary Analytical Data:

| | C (%) | H (%) |
|---|---|---|
| Found | 73.30 | 10.70 |
| Calcd. as $C_{47}H_{86}O_8$ | 73.01 | 10.43 |

Figure 18:
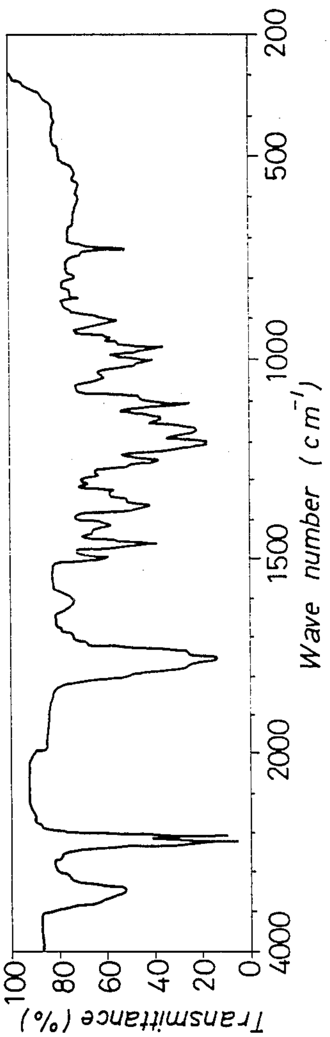

(3) Infrared absorption spectrum (by KBr-tablet method): The spectrum is shown in FIG. 18.

(4) Nuclear magnetic resonance spectrum of $^1H$: δ(in $CDCl_3$), ppm, 0.81 to 0.93(m): [—$\overset{|}{\underset{|}{C}}$—$CH_3$, (6H)], 1.25 to 1.64(m): [—$\overset{|}{\underset{|}{C}}$—$CH_2$—$\overset{|}{\underset{|}{C}}$—, (60H)], 2.29 to 2.43(m): [—$\underset{\overset{\|}{O}}{O C}$—$CH_2$—, and Ar—$\underset{\overset{\|}{O}}{O C}$—$CH_3$, (10H)], 7.16 to 7.44(m): [Ar—H, (3H)], 7.67(s): [Ar—$\underset{H}{\overset{|}{C}}\overset{\diagup O—}{\diagdown O—}$, (1H)].

EXAMPLE 16

Synthesis of 3,4-dioctadecanoyloxybenzylidene diacetate (the present substance No. 16)

In a 50 ml-flask, 10.2 g of 3,4-dioctadecanoylbenzaldehyde and 15.5 g of acetic anhydride were introduced, and after dissolving the 3,4-dioctadecanoylbenzaldehyde in acetic anhydride by heating the mixture to 60° to 70° C., one drop of concentrated sulfuric acid was added to the thus obtained solution, and the flask was shaken to initiate the reaction. A reaction exothermically proceeded to form a reaction mixture uniform and pale brown in colour. After shaking the reaction mixture for 2 min, the reaction mixture was cooled to room temperature and 100 ml of purified water were added to the reaction mixture. The thus separated white powdery crystals were collected by filtration and dried to obtain 11.73 g of a white powdery product in a yield of 99.8%. The product showed the following properties.

(1) Melting point: 81.0 to 82.0° C. (by capillary method)

(2) Elementary analytical data:

| | | C(%) | H(%) |
|---|---|---|---|
| Found | : | 73.00 | 10.60 |
| Calcd. as $C_{47}H_{86}O_8$ | : | 73.01 | 10.43 |

Figure 19:
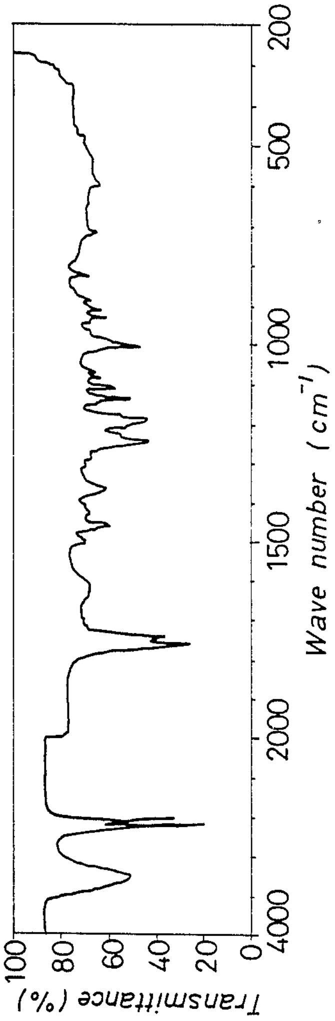

(3) Infrared absorption spectrum (by KBr-tablet method): The spectrum is shown in FIG. 19.

(4) Nuclear magnetic resonance spectrum of $^1H$: δ(in $CDCl_3$), ppm, 0.82 to 0.94(m): [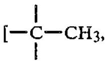, (6H)], 1.26 to 1.93(m): [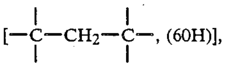, (60H)], 2.12(s): [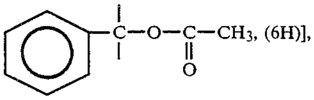, (6H)], 2.46 to 2.60(m): [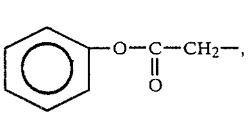, (4H)], 7.16 to 7.46(m): [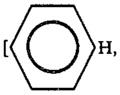, (3H)], 7.65(s): [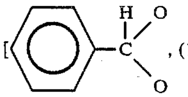, (1H)].

FORMULATION EXAMPLE 1

Preparation of powdery composition and capsular composition

Ten parts by weight of 3,4-dipropionyloxybenzylidene dipropionate (the present substance No. 4) 15 parts by weight of heavy magnesium oxide and 75 parts by weight of lactose were uniformly mixed and the mixture was pulverized to obtain a powdery composition, and by capsulating the thus formed powdery composition into capsules, a capsular composition was obtained.

FORMULATION EXAMPLE 2

Prearation of granular composition

Forty-five parts by weight of 3,4-didodecanoyloxybenzylidene didodecanoate (the present substance No. 5), 15 parts by weight of starch, 16 parts of lactose, 21 parts by weight of crystalline cellulose, 3 parts by weight of polyvinyl alcohol and 30 parts by weight of water were uniformly mixed, and the mixture was well kneaded.

Thereafter, the kneaded mixture was pulverized, shaped into granular form and dried. The thus dried material was sifted to obtain a granular composition.

FORMULATION EXAMPLE 3

Preparation of an injection

Ten parts by weight of 3,4-diacetoxybenzylidene diacetate (the present substance No. 1), 3 parts by weight of benzyl alcohol and 87 parts by weight of an aqueous physiological saline solution were mixed under heating, and the thus heated uniform mixture was sterilized to obtain an injection.

What is claimed is:

1. A process for producing a dialkanoyloxy-benzylidene dialkanoate of the formula (I):

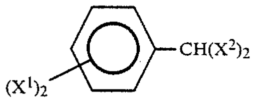

(I)

wherein $X^1$ and $X^2$ are an alkanoyloxy group having from 1 to 18 carbon atoms, which comprises the step:

(i) reacting a dihydroxybenzaldehyde with an alkanoic acid anhydride of the formula $(C_mH_{2m+1}—CO)_2O$, wherein m is an integer of 1 to 18 in the presence of base with heating or in the presence of strong acid.

2. A process for producing a dialkanoyloxy-benzylidene dialkanoate of the formula (I):

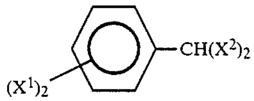

(I)

wherein $X^1$ and $X^2$ are, independently, an alkanoyloxy group having from 1 to 18 carbon atoms, which comprises the steps:

(i) reacting a dihydroxybenzaldehyde with an alkanoic acid anhydride of the formula $(C_nH_{2n+1}—CO)_2O$, wherein n is an integer of 1 to 18, to obtain a dialkanoyloxybenzaldehyde of the formula (II):

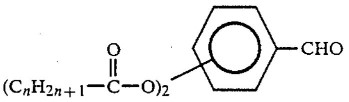

(II)

(ii) reacting said dialkanoyloxybenzaldehyde with an alkanoic acid anhydride of the formula $(C_mH_{2m+1}—CO)_2O$, wherein m is an integer of 1 to 18, in the presence of base with heating or in the presence of strong acid.

3. The process according to claims 1 or 2, wherein said base in one member selected from the group consisting of potassium hydroxide, sodium hydroxide, and sodium acetate.

4. The process according to claims 1 or 2, wherein said strong acid is one member selected from the group consisting of sulfuric acid, hydrochloric acid, and nitric acid.

* * * * *

UNITED STATES PATENT AND TRADEMARK OFFICE
CERTIFICATE OF CORRECTION

PATENT NO. : 4,841,097

DATED : JUNE 20, 1989

INVENTOR(S) : Hitoshi TAKITA et al

It is certified that error appears in the above-identified patent and that said Letters Patent is hereby corrected as shown below:

Column 1, lines 1-2, "dialkanoyloxybenzeylidene" should read --dialkanoyloxybenzylidene--.

Column 5, line 40, "rate" should read --rats--.

Column 8, line 42, "is is" should read --is in--; "0.1" should read --0.01--.

Column 11, line 31, "95°" should read --85°--.

Column 20, line 58, "said base in" should read --said base is--.

Signed and Sealed this

Eleventh Day of February, 1992

*Attest:*

HARRY F. MANBECK, JR.

*Attesting Officer*

*Commissioner of Patents and Trademarks*